US010245586B2

(12) United States Patent
Gilbert et al.

(10) Patent No.: US 10,245,586 B2
(45) Date of Patent: Apr. 2, 2019

(54) THREE-DIMENSIONAL FLUIDIC CHECK DEVICE

(71) Applicant: The Boeing Company, Chicago, IL (US)

(72) Inventors: Eric B. Gilbert, Seattle, WA (US); Timothy LeRoy Skilton, Bellevue, WA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 15/668,503

(22) Filed: Aug. 3, 2017

(65) Prior Publication Data
US 2019/0039066 A1    Feb. 7, 2019

(51) Int. Cl.
| F15C 1/02 | (2006.01) |
| B01L 3/00 | (2006.01) |
| G01N 27/27 | (2006.01) |
| B01L 7/00 | (2006.01) |
| B01F 15/02 | (2006.01) |

(52) U.S. Cl.
CPC .... *B01L 3/502715* (2013.01); *B01F 15/0203* (2013.01); *B01L 3/502707* (2013.01); *B01L 3/502738* (2013.01); *B01L 7/52* (2013.01); *G01N 27/27* (2013.01)

(58) Field of Classification Search
CPC ......... B01L 5/502715; B01L 5/502707; B01L 5/502738; B01L 7/52; B01F 15/0203; G01N 27/27
USPC .............. 137/833, 808, 809, 813, 330, 511; 251/126, 127, 366
See application file for complete search history.

(56) References Cited

U.S. PATENT DOCUMENTS

| 1,329,559 | A | * | 2/1920 | Tesla ......................... F15C 1/00 137/842 |
| 3,372,649 | A | * | 3/1968 | Webber ................... E21B 37/10 417/307 |
| 3,640,845 | A | * | 2/1972 | Ripley ...................... F16J 15/44 137/808 |
| 4,557,295 | A | * | 12/1985 | Holmes ..................... F15C 1/16 137/809 |
| 5,145,256 | A | * | 9/1992 | Wiemers ................. B01F 5/061 137/808 |
| 5,265,636 | A | * | 11/1993 | Reed ........................ F15C 1/146 137/14 |

(Continued)

FOREIGN PATENT DOCUMENTS

EP    2677240 A2    12/2013

OTHER PUBLICATIONS

Thompson et al., "Numerical Investigation of Multistage Tesla Valves", ASME Journal of Fluids Engineering, May 12, 2014, 9 pages.

(Continued)

*Primary Examiner* — Minh Le
(74) *Attorney, Agent, or Firm* — Yee & Associates, P.C.

(57) ABSTRACT

A monolithic three-dimensional fluidic check device is presented. The monolithic three-dimensional fluidic check device comprises a housing surrounding a fluidic flow path and having a first opening at a first end of the housing and a second opening at a second end of the housing, and an elongated center body positioned within and extending along the fluidic flow path. The elongated center body is stationary relative to a flow of fluid.

14 Claims, 11 Drawing Sheets

(56) References Cited

U.S. PATENT DOCUMENTS

| | | | | |
|---|---|---|---|---|
| 7,909,094 B2* | 3/2011 | Schultz | ............... | E21B 36/02 |
| | | | | 137/833 |
| 9,038,652 B1* | 5/2015 | Henry | ............... | F16K 15/20 |
| | | | | 137/223 |
| 9,169,855 B1* | 10/2015 | Dyson | ............... | F15C 5/00 |
| 9,903,536 B2* | 2/2018 | Lin | ............... | F17D 1/16 |
| 2009/0308472 A1* | 12/2009 | Harman | ............... | B01F 5/0615 |
| | | | | 137/808 |
| 2012/0097280 A1* | 4/2012 | Hallberg | ............... | B01F 5/0057 |
| | | | | 137/808 |
| 2013/0140038 A1* | 6/2013 | Fripp | ............... | E21B 34/08 |
| | | | | 166/373 |
| 2013/0341430 A1 | 12/2013 | Hall et al. | | |
| 2015/0337878 A1* | 11/2015 | Schlosser | ............... | F42B 10/42 |
| | | | | 181/213 |

OTHER PUBLICATIONS

"Tesla Valved Pulse Jet Leaf Blower", halfbakery, accessed Jul. 26, 2017, 3 pages. http://www.halfbakery.com/idea/Tesla_20Valved_20Pulse_20Jet_20Leaf_20Blower.

* cited by examiner

THREE-DIMENSIONAL FLUIDIC CHECK DEVICE

BACKGROUND INFORMATION

1. Field

The present disclosure relates generally to fluid flow, and more particularly, to valves for controlling fluid flow. Still more particularly, the present disclosure relates to three-dimensional fluidic check devices.

2. Background

Valves are devices that control the flow of fluid through a system. Valves control the flow of fluid by completely or partially opening or closing pathways for a fluid. Valves are used in both industrial processes and residential processes. A plurality of conventional valve designs exists. One type of valve is a check valve.

A check valve allows a fluid to flow in one direction while hindering the flow of fluid in the opposite direction. A check valve may be considered a one-way valve.

Conventional three-dimensional check valves include ball valves, flapper valves, and shuttle valves, each having moving parts. Moving parts that are subjected to cycling can wear out or can fail to move when directed. Inspection and maintenance may be implemented for conventional three-dimensional check valves having moving parts. Therefore, it would be desirable to have a method and apparatus that takes into account at least some of the issues discussed above, as well as other possible issues.

SUMMARY

An illustrative embodiment of the present disclosure provides a monolithic three-dimensional fluidic check device comprising a housing and an elongated center body. The housing surrounds a fluidic flow path and having a first opening at a first end of the housing and a second opening at a second end of the housing. The elongated center body is positioned within and extends along the fluidic flow path. The elongated center body is stationary relative to a flow of fluid.

A further illustrative embodiment of the present disclosure provides a three-dimensional fluidic check device comprising a housing and an elongated center body. The housing contains a fluidic flow path formed by the housing and the elongated center body. The housing comprises a first plurality of fins extending from the housing into the fluidic flow path. The elongated center body is surrounded by the fluidic flow path. The elongated center body comprises a second plurality of fins extending from the elongated center body into the fluidic flow path. The first plurality of fins and the second plurality of fins are configured to allow flow of a fluid in a flow direction through the housing and to restrict flow of the fluid in a checked direction.

Another illustrative embodiment of the present disclosure provides a method. A fluid flows through a fluidic flow path of a three-dimensional fluidic check device from a first opening at a first end of a housing of the three-dimensional fluidic check device to a second opening at a second end of the housing. The fluid is checked from moving from the second opening to the first opening by directing the momentum of the fluid using only the housing and an elongated center body positioned within and extending along the fluidic flow path to restrict a flow of the fluid from the second opening to the first opening.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

DETAILED DESCRIPTION

The illustrative embodiments recognize and take into account one or more different considerations. For example, the illustrative embodiments recognize and take into account that three-dimensional check valves are more efficient than two-dimensional check valves. The illustrative embodiments recognize and take into account that two-dimensional check valves may have additional disadvantages. The illustrative embodiments recognize and take into account that a two-dimensional Tesla check valve has an undesirably large size for some uses. The illustrative embodiments recognize and take into account that a two-dimensional Tesla check valve has an undesirably high cost of fabrication. The illustrative embodiments recognize and take into account that a Tesla check valve provides a two-dimensional fluid flow.

The illustrative embodiments recognize and take into account that check valves may be installed in locations having limited access. The illustrative embodiments recognize and take into account that traditional check valves may require inspection. For example, the illustrative embodiments recognize and take into account that a traditional check valve may require regular inspection (e.g., of moving parts). For example, check valves may be installed in an aircraft, and as such, may require inspection in accordance with a maintenance program.

Figure 1:
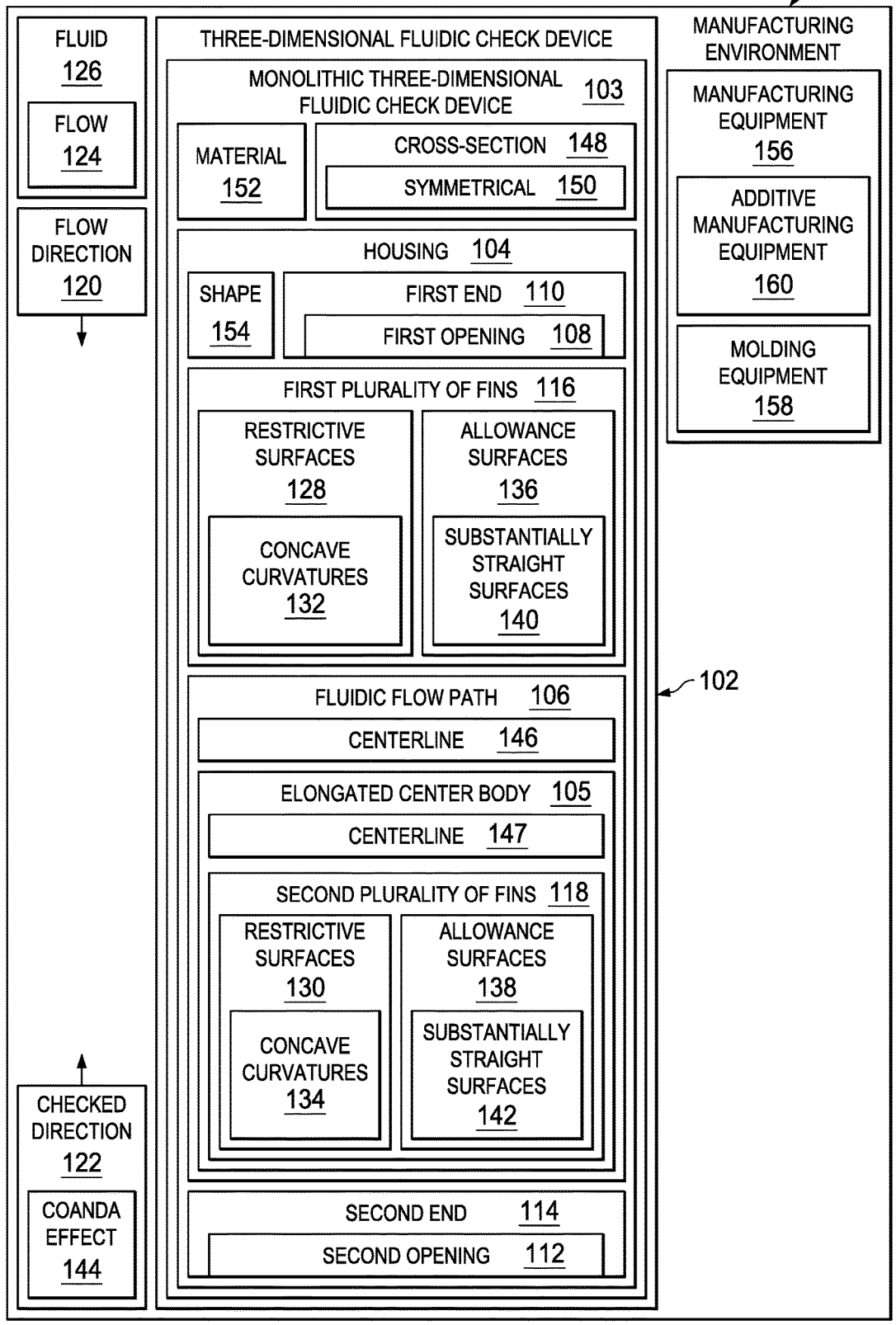
FIG. 1 is an illustration of a block diagram of a manufacturing environment in accordance with an illustrative embodiment.

With reference now to the Figures and, in particular, with reference to FIG. 1, an illustration of a block diagram of a manufacturing environment is depicted in accordance with an illustrative embodiment. Manufacturing environment 100 is an environment in which three-dimensional fluidic check device 102 may be manufactured. In some illustrative examples, three-dimensional fluidic check device 102 is monolithic. When three-dimensional fluidic check device 102 is monolithic, three-dimensional fluidic check device 102 is monolithic three-dimensional fluidic check device 103. Components of monolithic three-dimensional fluidic check device 103 are integrally formed. For example, monolithic three-dimensional fluidic check device 103 may be a solid, one-piece structure that is void of sub-assemblies.

Three-dimensional fluidic check device 102 comprises housing 104 and elongated center body 105. Three-dimensional fluidic check device 102 comprises housing 104 surrounding fluidic flow path 106 and having first opening 108 at first end 110 of housing 104 and second opening 112 at second end 114 of housing 104, and elongated center body 105 positioned within and extending along fluidic flow path 106.

Monolithic three-dimensional fluidic check device 103 includes housing 104 and elongated center body 105 integrally formed to create fluidic flow path 106. In some illustrative examples, fluidic flow path 106 has no other structures within fluidic flow path 106.

In some illustrative examples, elongated center body 105 may be formed with portions attached to housing 104. In these illustrative examples, three-dimensional fluidic check device 102 is monolithic three-dimensional fluidic check device 103.

In other illustrative examples, elongated center body 105 and housing 104 may be formed separately and joined using any desirable method. Once joined to housing 104, elongated center body 105 is stationary within housing 104.

Monolithic three-dimensional fluidic check device 103 is an implementation of three-dimensional fluidic check device 102. Descriptions of features of three-dimensional fluidic check device 102 below also describe features of monolithic three-dimensional fluidic check device 103.

In three-dimensional fluidic check device 102, housing 104 comprises first plurality of fins 116 extending from housing 104 into fluidic flow path 106. First plurality of fins 116 is integral to housing 104. By being integral to housing 104, first plurality of fins 116 are formed as part of housing 104. In three-dimensional fluidic check device 102, elongated center body 105 comprises second plurality of fins 118 extending from elongated center body 105 into fluidic flow path 106. Second plurality of fins 118 is integral to elongated center body 105. By being integral to elongated center body 105, second plurality of fins 118 is formed as part of elongated center body 105.

First plurality of fins 116 and second plurality of fins 118 are configured to create flow direction 120 from first end 110 to second end 114 and checked direction 122 from second end 114 to first end 110. First plurality of fins 116 and second plurality of fins 118 are configured to allow flow 124 of fluid 126 in flow direction 120 through housing 104. First plurality of fins 116 and second plurality of fins 118 are configured to restrict flow 124 of fluid 126 in checked direction 122. Elongated center body 105 is stationary relative to flow 124 of fluid 126.

Each of first plurality of fins 116 and each of second plurality of fins 118 has a respective restrictive surface restricting flow 124 of fluid 126 in checked direction 122. First plurality of fins 116 has restrictive surfaces 128. In one illustrative example, each of restrictive surfaces 128 has the same geometry. In other illustrative examples, restrictive surfaces 128 include a plurality of geometries.

Second plurality of fins 118 has restrictive surfaces 130. In one illustrative example, each of restrictive surfaces 130 has the same geometry. In other illustrative examples, restrictive surfaces 130 include a plurality of geometries.

In some illustrative examples, each restrictive surface is a concave curvature. In these illustrative examples, restrictive surfaces 128 are concave curvatures 132. In these illustrative examples, restrictive surfaces 130 are concave curvatures 134. For example, concave curvatures 134 may have a curvature that generally opens towards centerline 146.

First plurality of fins 116 and second plurality of fins 118 are configured to control pressure drops through three-dimensional fluidic check device 102. A pressure drop is a difference in pressure between outgoing fluid and incoming fluid in a specified direction. In some illustrative examples, first plurality of fins 116 and second plurality of fins 118 are configured to minimize or reduce the pressure drop in flow direction 120 while maximizing or increasing the pressure drop in checked direction 122 depending on the Reynolds number and viscosity of fluid 126 passing though three-dimensional fluidic check device 102. In some illustrative examples, restrictive surfaces 128 and restrictive surfaces 130 are configured to minimize or reduce the pressure drop in flow direction 120 while maximizing or increasing the pressure drop in checked direction 122 depending on the Reynolds number and viscosity of fluid 126 passing though three-dimensional fluidic check device 102.

In some illustrative examples, each of first plurality of fins 116 and each of second plurality of fins 118 has a respective concave curvature facing second end 114. In these illustrative examples, concave curvatures 132 and concave curvatures 134 face second end 114.

Each of first plurality of fins 116 and each of second plurality of fins 118 has a respective allowance surface allowing flow 124 of fluid 126 in flow direction 120. First plurality of fins 116 has allowance surfaces 136. In one illustrative example, each of allowance surfaces 136 has the same geometry. In other illustrative examples, allowance surfaces 136 include a plurality of geometries.

Second plurality of fins 118 has allowance surfaces 138. In one illustrative example, each of allowance surfaces 138 has the same geometry. In other illustrative examples, allowance surfaces 138 include a plurality of geometries.

In some illustrative examples, each allowance surface is a substantially straight surface. In these illustrative examples, allowance surfaces 136 are substantially straight surfaces 140. In these illustrative examples, allowance surfaces 138 are substantially straight surfaces 142.

In some illustrative examples, each of first plurality of fins 116 and each of second plurality of fins 118 has a respective substantially straight surface facing first end 110. In these illustrative examples, substantially straight surfaces 140 and substantially straight surfaces 142 face first end 110.

In some illustrative examples, first plurality of fins 116 overlaps second plurality of fins 118. In some other illustrative examples, a gap is present between first plurality of fins 116 and second plurality of fins 118.

In three-dimensional fluidic check device 102, fluidic flow path 106 is formed and bounded by housing 104 including first plurality of fins 116 and elongated center body 105 including second plurality of fins 118. The geometry of housing 104 and the geometry of elongated center body 105 are configured to provide fluidic flow path 106. The geometry of housing 104 and the geometry of elongated center body 105 are configured based on properties of fluid 126. The geometry of first plurality of fins 116 and the geometry of second plurality of fins 118 are configured to provide flow 124 of fluid 126 and generate Coanda effect 144.

Coanda effect 144 biases flow 124 of fluid 126 in checked direction 122 towards at least one of restrictive surfaces 130 or restrictive surfaces 128 of three-dimensional fluidic check device 102. The geometry of first plurality of fins 116 and the geometry of second plurality of fins 118 are configured to bias flow 124 of fluid 126 in checked direction 122 towards at least one of restrictive surfaces 130 or restrictive surfaces 128 of three-dimensional fluidic check device 102.

As used herein, the phrase "at least one of," when used with a list of items, means different combinations of one or more of the listed items may be used, and only one of each item in the list may be needed. In other words, "at least one of" means any combination of items and number of items may be used from the list, but not all of the items in the list are required. The item may be a particular object, a thing, or a category.

For example, "at least one of item A, item B, or item C" may include, without limitation, item A, item A and item B, or item B. This example also may include item A, item B, and item C, or item B and item C. Of course, any combination of these items may be present. In other examples, "at least one of" may be, for example, without limitation, two of item A, one of item B, and ten of item C; four of item B and seven of item C; or other suitable combinations.

Due to Coanda effect 144, the geometry of first plurality of fins 116, and the geometry of second plurality of fins 118, additional structures to direct fluid 126 are not present in fluidic flow path 106. Flow 124 of fluid 126 in checked direction 122 is biased towards at least one of restrictive surfaces 130 or restrictive surfaces 128 of three-dimensional fluidic check device 102 using only the geometry of elongated center body 105 and the geometry of housing 104.

Three-dimensional fluidic check device 102 has a first distance from a point of one of first plurality of fins 116 to elongated center body 105 measured perpendicular to centerline 146 extending through fluidic flow path 106. Three-dimensional fluidic check device 102 has a second distance from a point of one of second plurality of fins 118 to housing 104 measured perpendicular to centerline 146 extending through fluidic flow path 106.

In some illustrative examples, the first distance and the second distance are the same. In some illustrative examples, a ratio of the first distance to the second distance is configured to produce Coanda effect 144 for fluid 126 moving from second end 114 to first end 110 within the fluidic flow path 106.

Three-dimensional fluidic check device 102 has a first measurement from a point of one of first plurality of fins 116 to centerline 147 of elongated center body 105 and a second measurement from a point of one of second plurality of fins 118 to centerline 147 of elongated center body 105. In some illustrative examples, the difference between the first measurement and the second measurement is negative. When the difference between the first measurement and the second measurement is negative, first plurality of fins 116 overlaps second plurality of fins 118.

In some illustrative examples, the difference between the first measurement and the second measurement is positive. When the difference between the first measurement and the second measurement is positive, a gap is present between first plurality of fins 116 and second plurality of fins 118.

Three-dimensional fluidic check device 102 has cross-section 148. In some illustrative examples, cross-section 148 of three-dimensional fluidic check device 102 through first opening 108 and second opening 112 is symmetrical 150 about centerline 146 extending through fluidic flow path 106.

Three-dimensional fluidic check device 102 is formed of any desirable type of material 152. Material 152 is selected based on a type of fluid 126. Material 152 is selected based on flow 124. In some illustrative examples, housing 104 and elongated center body 105 are formed of material 152 configured to allow for changing shape 154 of housing 104.

In some illustrative examples, material 152 is a polymeric material. In some illustrative examples, material 152 is an elastomeric material such as silicone rubber. When material 152 is flexible, acceptable changes to shape 154 are dependent upon the internal geometries of housing 104 and elongated center body 105. In some illustrative examples, internal geometries of housing 104 and elongated center body 105 may be configured based on expected changes to shape 154. In some illustrative examples, housing 104 and elongated center body 105 are flexible, and fabricated taking into account design guidelines for at least one of the flexible material, the fluid to flow through three-dimensional fluidic check device 102, expected changes to shape 154, or any other design guidelines.

When material 152 is flexible, elongated center body 105 remains stationary relative to flow of 124 of fluid 126. Flow 124 of fluid 126 does not move elongated center body 105. Flow direction 120 and checked direction 122 are formed without movement of elongated center body 105.

Material 152, rigid or flexible, may be formed using any desirable method. In some illustrative examples, material 152 is formed into three-dimensional fluidic check device 102 using additive manufacturing. For example, three-dimensional fluidic check device 102 may be printed on three-dimensional printers. In some illustrative examples, material 152 is formed into three-dimensional fluidic check device 102 by molding.

In some illustrative examples, three-dimensional fluidic check device 102 comprises housing 104 containing fluidic flow path 106 formed by housing 104 and elongated center body 105, and elongated center body 105 surrounded by fluidic flow path 106. In these illustrative examples, housing 104 comprises first plurality of fins 116 extending from housing 104 into fluidic flow path 106. In these illustrative examples, elongated center body 105 comprises second plurality of fins 118 extending from elongated center body 105 into fluidic flow path 106, wherein first plurality of fins 116 and second plurality of fins 118 are configured to allow flow 124 of fluid 126 in flow direction 120 through housing 104 and to restrict flow 124 of fluid 126 in checked direction 122.

Manufacturing equipment 156 is used to form three-dimensional fluidic check device 102. In some illustrative examples, housing 104 and elongated center body 105 are formed separately. In other illustrative examples, housing 104 and elongated center body 105 are formed together.

Manufacturing equipment 156 takes any desirable form. In one illustrative example, manufacturing equipment 156 is molding equipment 158. When manufacturing equipment 156 is molding equipment 158, housing 104 and elongated center body 105 may be formed separately. When housing 104 and elongated center body 105 are formed separately, elongated center body 105 is later secured within housing 104 using fasteners, adhesive, or any other desirable method of securing elongated center body 105 within housing 104. In other illustrative examples, molding equipment 158 may include removable molding inserts such that elongated center body 105 is molded within housing 104.

In another illustrative example, manufacturing equipment 156 is additive manufacturing equipment 160. Additive manufacturing equipment 160 may manufacture elongated center body 105 within housing 104.

The illustration of manufacturing environment 100 in FIG. 1 is not meant to imply physical or architectural limitations to the manner in which an illustrative embodiment may be implemented. Other components, in addition to or in place of the ones illustrated, may be used. Some components may be unnecessary. Also, the blocks are presented to illustrate some functional components. One or more of these blocks may be combined, divided, or combined and divided into different blocks when implemented in an illustrative embodiment.

Three-dimensional fluidic check device 102 is connected to a system using any desirable method and using any desirable features. In some illustrative examples, three-dimensional fluidic check device 102 is connected to a system at first end 110 and second end 114.

In one illustrative example, three-dimensional fluidic check device 102 includes a number of end connectors for joining three-dimensional fluidic check device 102 to a system. As used herein, "a number of items" is one of more items. For example, a number of end connectors is one or more end connectors. The number of end connectors may take any desirable form. For example, threads (not depicted) may be on at least one of first end 110 or second end 114 of housing 104. In another example, fasteners, e.g., bolts (not depicted) may be associated with at least one of first end 110 or second end 114 of housing 104 to join three-dimensional fluidic check device 102 to a fluid system.

In some illustrative examples, three-dimensional fluidic check device 102 may be inserted within an existing conduit. In these illustrative examples, three-dimensional fluidic check device 102 is secured within the existing conduit using any desirable method. For example, three-dimensional fluidic check device 102 is secured within the existing conduit using at least one of adhesive, welding, fasteners, interference fit, or any other method of securing. When three-dimensional fluidic check device 102 is secured within an existing conduit, the outer shell of the existing conduit can react the internal pressures just as conventional systems do with the added benefit of the three-dimensional fluidic check device 102 inside the system.

By including the three-dimensional fluidic check device 102 as a check feature into a pre-existing conduit, the overall number of parts in the system can be reduced. By including the three-dimensional fluidic check device 102 as a check feature into a pre-existing conduit, the overall length of the system can be reduced because a check valve is no longer installed up stream or downstream of the conduit. When three-dimensional fluidic check device 102 is flexible, three-dimensional fluidic check device 102 may be placed within an existing flexible conduit and glued into place.

Figure 2:
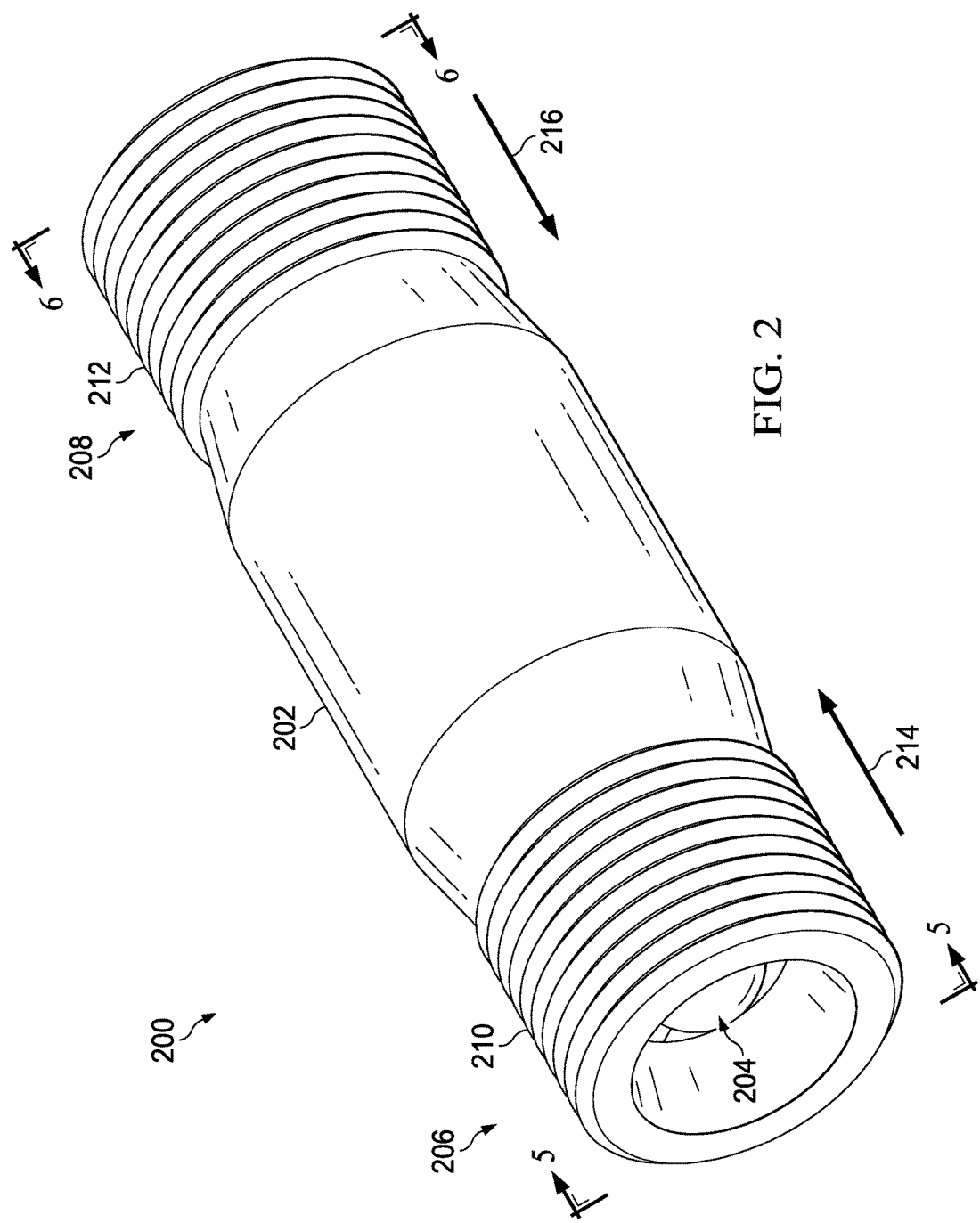
FIG. 2 is an illustration of an external view of a three-dimensional fluidic check device in accordance with an illustrative embodiment.

Turning now to FIG. 2, an illustration of an external view of a three-dimensional fluidic check device is depicted in accordance with an illustrative embodiment. Three-dimensional fluidic check device 200 is a physical implementation of three-dimensional fluidic check device 102 of FIG. 1.

Three-dimensional fluidic check device 200 comprises housing 202 and elongated center body 204. In some illustrative examples, three-dimensional fluidic check device 200 is a monolithic three-dimensional fluidic check device. In these illustrative examples, housing 202 and elongated center body 204 are integrally formed.

In some illustrative examples, housing 202 is a monolithic housing. In some illustrative examples, elongated center body 204 is a monolithic elongated center body.

Housing 202 has first end 206 and second end 208. In this illustrative example, threads 210 are present on first end 206 of housing 202. In this illustrative example, threads 212 are present on second end 208 of housing 202.

Elongated center body 204 is joined to housing 202 such that elongated center body 204 is stationary within housing 202. Elongated center body 204 is joined to housing 202 such that elongated center body 204 is stationary relative to a flow of fluid (not depicted). In some illustrative examples, elongated center body 204 and housing 202 are designed to have connecting ribs. In these illustrative examples, elongated center body 204, housing 202, and connecting ribs may each be formed by additive manufacturing. In other illustrative examples, elongated center body 204 and housing 202 are formed separately and then joined together using any desirable method.

Three-dimensional fluidic check device 200 is configured such that a flow of fluid (not depicted) is allowed in flow direction 214. Three-dimensional fluidic check device 200 is configured such that a flow of fluid (not depicted) is restricted in checked direction 216.

Figure 3:
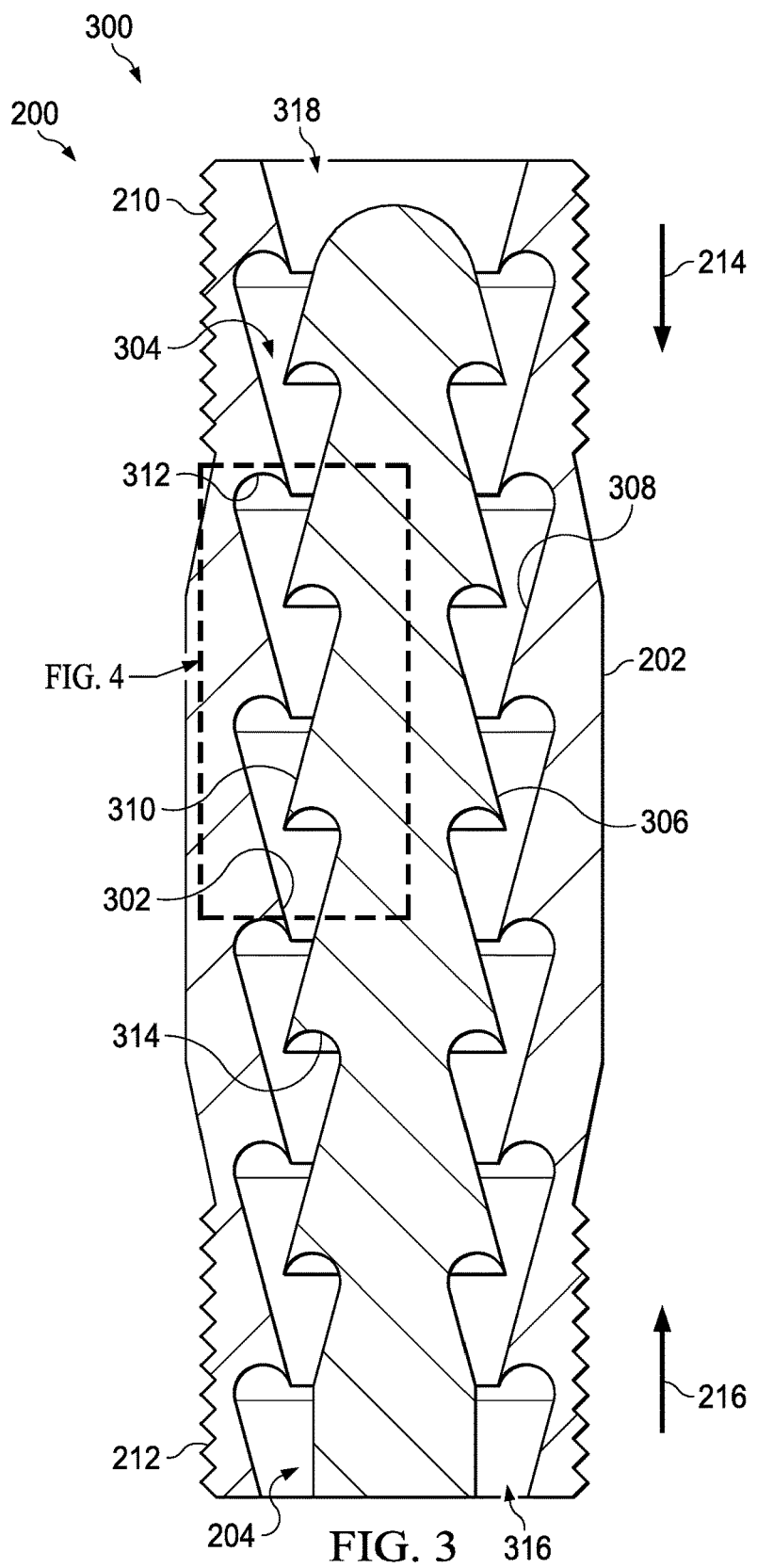
FIG. 3 is an illustration of a cross-sectional view of a three-dimensional fluidic check device in accordance with an illustrative embodiment.

Turning now to FIG. 3, an illustration of a cross-sectional view of a three-dimensional fluidic check device is depicted in accordance with an illustrative embodiment. View 300 is a cross-sectional view of three-dimensional fluidic check device 200 of FIG. 2.

Housing 202 of three-dimensional fluidic check device 200 has first plurality of fins 302 extending from housing 202 into fluidic flow path 304. First plurality of fins 302 is integral to housing 202. Fluidic flow path 304 is formed by housing 202 and elongated center body 204. Housing 202 contains fluidic flow path 304. Elongated center body 204 is surrounded by fluidic flow path 304.

Fluidic flow path 304 is formed and bounded by housing 202 including first plurality of fins 302 and elongated center body 204 including second plurality of fins 306. As depicted, no other structures are within fluidic flow path 304.

Elongated center body 204 comprises second plurality of fins 306 extend from elongated center body 204 into fluidic flow path 304. Second plurality of fins 306 is integral to elongated center body 204. First plurality of fins 302 and second plurality of fins 306 are configured to allow flow of a fluid (not depicted) in flow direction 214 through housing 202 and to restrict flow of the fluid (not depicted) in checked direction 216. As depicted, first plurality of fins 302 overlaps second plurality of fins 306.

First plurality of fins 302 and second plurality of fins 306 are configured to control pressure drops through three-dimensional fluidic check device 200. In some illustrative examples, first plurality of fins 302 and second plurality of fins 306 are configured to minimize the pressure drop in flow direction 214 while maximizing the pressure drop in checked direction 216 depending on the Reynolds number and viscosity of a fluid (not depicted) passing though three-dimensional fluidic check device 200.

First plurality of fins 302 has allowance surfaces 308. As depicted, allowance surfaces 308 are substantially straight surfaces in cross-sectional view, view 300. First plurality of fins 302 are three-dimensional features. In a different view, such as a top view from flow direction 214, allowance surfaces 308 may be described as inverted conical surfaces.

In other illustrative examples, allowance surfaces 308 may have a constant curvature, a varying curvature, or other non-linear shape in a cross-sectional view, view 300. Allowance surfaces 308 allow the flow of fluid in flow direction 214. As depicted, allowance surfaces 308 are all substantially the same. In some other illustrative examples, allowance surfaces 308 may have a plurality of geometries. In some illustrative examples, allowance surfaces 308 may have different geometries moving from first end 206 to second end 208. For example, an angle of the allowance surfaces 308 relative to housing 202 may change moving from first end 206 to second end 208.

Second plurality of fins 306 has allowance surfaces 310. As depicted, allowance surfaces 310 are substantially straight surfaces in cross-sectional view, view 300. Second plurality of fins 306 are three-dimensional features. In a different view, such as a top view from flow direction 214, allowance surfaces 310 may be described as conical surfaces.

In other illustrative examples, allowance surfaces 310 may have a constant curvature, a varying curvature, or other non-linear shape in a cross-sectional view, view 300. Allowance surfaces 310 allow the flow of fluid in flow direction 214. As depicted, allowance surfaces 310 are all substantially the same. In some other illustrative examples, allowance surfaces 310 may have a plurality of geometries. In some illustrative examples, allowance surfaces 310 may have different geometries moving from first end 206 to second end 208. For example, an angle of allowance surfaces 310 relative to housing 202 may change moving from first end 206 to second end 208.

In some illustrative examples, allowance surfaces 308 and allowance surfaces 310 are substantially the same in cross-sectional view. Allowance surfaces 308 and allowance surfaces 310 are configured to work together to allow for a flow of fluid.

First plurality of fins 302 has restrictive surfaces 312. As depicted, restrictive surfaces 312 are concave curvatures facing second end 208 of housing 202. Restrictive surfaces 312 restrict the flow of fluid in checked direction 216. As depicted, restrictive surfaces 312 are all substantially the same. In some other illustrative examples, restrictive surfaces 312 may have a plurality of geometries. In some illustrative examples, restrictive surfaces 312 may have different geometries moving from first end 206 to second end 208.

Second plurality of fins 306 has restrictive surfaces 314. As depicted, restrictive surfaces 314 are concave curvatures facing second end 208 of housing 202. Restrictive surfaces 314 restrict the flow of fluid in checked direction 216. As depicted, restrictive surfaces 314 are all substantially the same. In some other illustrative examples, restrictive surfaces 314 may have a plurality of geometries. In some illustrative examples, restrictive surfaces 314 may have different geometries moving from first end 206 to second end 208.

Restrictive surfaces 312 and restrictive surfaces 314 are configured to control pressure drops in three-dimensional fluidic check device 200. In some illustrative examples, restrictive surfaces 312 and restrictive surfaces 314 are configured to minimize the pressure drop in flow direction 214 while maximizing the pressure drop in checked direction 216 depending on the Reynolds number and viscosity of a fluid (not depicted) passing though three-dimensional fluidic check device 200.

Restrictive surfaces 312 and restrictive surfaces 314 are configured to generate the Coanda effect in fluid flow from second end 208 to first end 206. The Coanda effect directs the momentum of the fluid. Directing the momentum of the fluid using housing 202 and elongated center body 204 positioned within and extending along fluidic flow path 304 restricts the flow of the fluid from second opening 316 to first opening 318.

The Coanda effect biases the flow of fluid (not depicted) in checked direction 216 towards at least one of restrictive surfaces 312 or restrictive surfaces 314 of three-dimensional fluidic check device 200. The geometry of first plurality of fins 302 and the geometry of second plurality of fins 306 are configured to bias the flow of the fluid (not depicted) in checked direction 216 towards at least one of restrictive surfaces 312 or restrictive surfaces 314 of three-dimensional fluidic check device 200.

Due to the Coanda effect, the geometry of first plurality of fins 302, and the geometry of second plurality of fins 306, additional structures to direct fluid are not present in fluidic flow path 304. Flow of fluid in checked direction 216 is biased towards at least one of restrictive surfaces 312 or restrictive surfaces 314 of three-dimensional fluidic check device 200 using only the geometry of elongated center body 204 and the geometry of housing 202.

Figure 4:
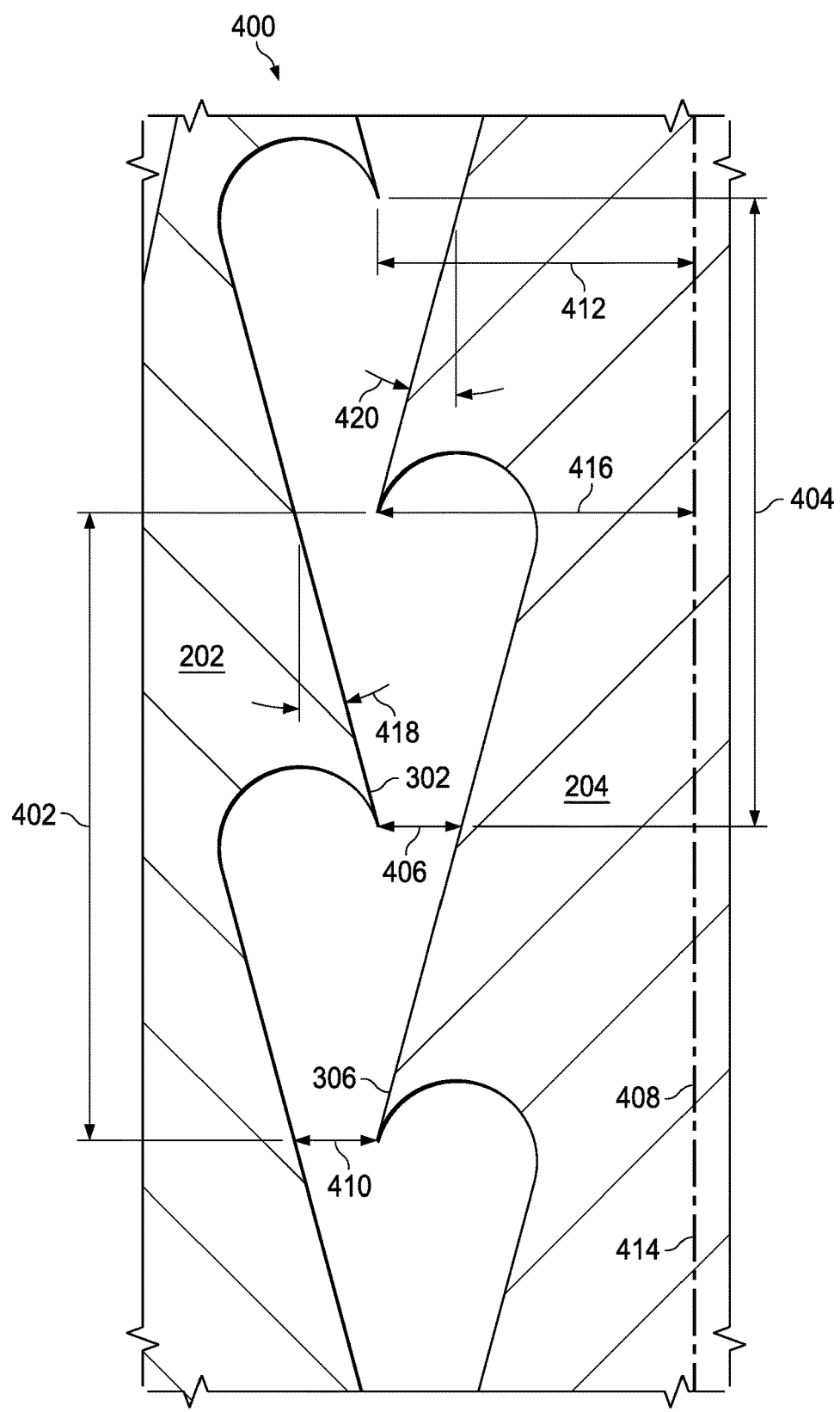
FIG. 4 is an illustration of a cross-sectional view of a three-dimensional fluidic check device in accordance with an illustrative embodiment.

Turning now to FIG. 4, an illustration of a cross-sectional view of a three-dimensional fluidic check device is depicted in accordance with an illustrative embodiment. View 400 is a view of first plurality of fins 302 and second plurality of fins 306 within box 4 of FIG. 3.

The geometry of first plurality of fins 302 and the geometry of second plurality of fins 306 are configured based on the desired flow of a fluid, the type of fluid, and generating the Coanda effect. First plurality of fins 302 and second plurality of fins 306 have a plurality of variables that may be changed.

Length 402 is a distance between points of first plurality of fins 302. In this illustrative example, each of first plurality of fins 302 has the same geometry. Length 402 for each of first plurality of fins 302 is the same. Length 402 may be referred to as a "base unit length."

Length 404 is a distance between points of second plurality of fins 306. In this illustrative example, each of second plurality of fins 306 has the same geometry. Length 404 for each of second plurality of fins 306 is the same. Length 404 may be referred to as a "base unit length."

In this illustrative example, length 402 and length 404 are substantially the same. In some illustrative examples, length 402 and length 404 may be different.

First distance 406 is from a point of one of first plurality of fins 302 to elongated center body 204 measured perpendicular to centerline 408 extending through fluidic flow path 304. Second distance 410 is from a point of one of second plurality of fins 306 to housing 202 measured perpendicular to centerline 408 extending through fluidic flow path 304. In some illustrative examples, first distance 406 is substantially the same as second distance 410.

A difference between first measurement 412 from a point of one of first plurality of fins 302 to centerline 414 of elongated center body 204 and second measurement 416 from a point of one of second plurality of fins 306 to centerline 414 of elongated center body 204 is variable. In some illustrative examples, the difference between first measurement 412 and second measurement 416 is negative. When the difference is negative, first plurality of fins 302 overlaps second plurality of fins 306, as depicted. In other illustrative examples, such as in FIG. 9, the difference between first measurement 412 and second measurement 416 is positive.

As depicted, centerline 408 extending through fluidic flow path 304 and centerline 414 of elongated center body 204 are the same. In this illustrative example, elongated center body 204 is centered within fluidic flow path 304. However, in other non-depicted illustrative examples, centerline 408 and centerline 414 may be different when elongated center body 204 is not completely centered within fluidic flow path 304.

Each of allowance surfaces 308 of first plurality of fins 302 has angle 418. Angle 418 affects the flow of fluid through three-dimensional fluidic check device 200. Angle 418 also affects the overlap of first plurality of fins 302 and second plurality of fins 306. As depicted, angle 418 is approximately 15 degrees. Angle 418 is selected taking into account the characteristics of the fluid and the characteristics of the flow including the viscosity of the fluid, temperature of the fluid, speed of flow, Reynolds number of the fluid, and any other desirable fluid or flow features.

As depicted, each of allowance surfaces 308 has the same angle, angle 418. In other non-depicted examples, at least one of allowance surfaces 308 has a different angle than angle 418. In some non-depicted illustrative examples, each of allowance surfaces 308 has a different angle from each other allowance surface of allowance surfaces 308.

Each of allowance surfaces 310 of second plurality of fins 306 has angle 420. Angle 420 affects the flow of fluid through three-dimensional fluidic check device 200. Angle 420 also affects the overlap of first plurality of fins 302 and second plurality of fins 306. As depicted, angle 420 is approximately 15 degrees. Angle 420 is selected taking into account the characteristics of the fluid and the characteristics of the flow including the viscosity of the fluid, temperature of the fluid, speed of flow, Reynolds number of the fluid, and any other desirable fluid or flow features.

As depicted, each of allowance surfaces 310 has the same angle, angle 420. In other non-depicted examples, at least one of allowance surfaces 310 has a different angle than angle 420. In some non-depicted illustrative examples, each of allowance surfaces 310 has a different angle from each other allowance surface of allowance surfaces 310.

Figure 5:
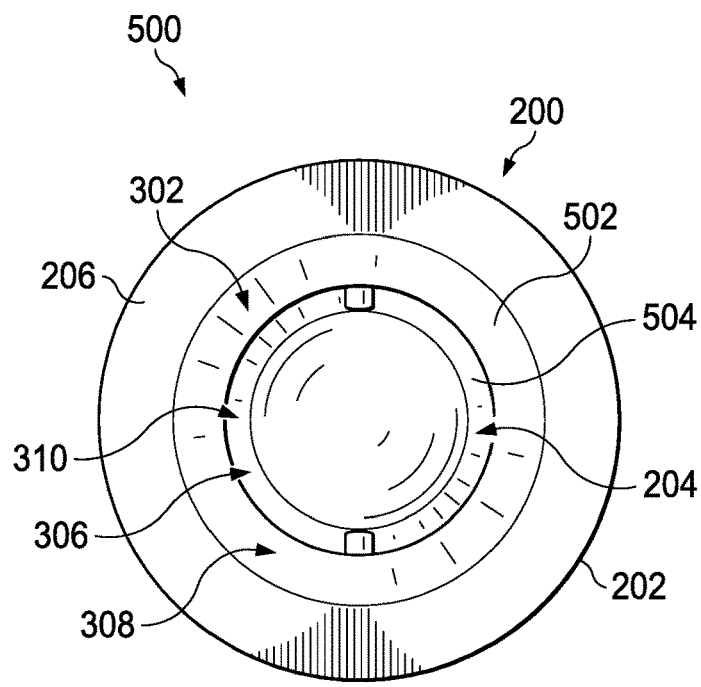
FIG. 5 is an illustration of a top view of a three-dimensional fluidic check device in accordance with an illustrative embodiment.

Turning now to FIG. 5, an illustration of a top view of a three-dimensional fluidic check device is depicted in accordance with an illustrative embodiment. View 500 is a view of three-dimensional fluidic check device 200 from direction 5 of FIG. 2. View 500 is a view looking into first end 206 towards second end 208.

As can be seen in view 500, fluidic flow path 304 is not a straight path from first end 206 to second end 208. First plurality of fins 302 overlaps second plurality of fins 306 creating a circuitous fluidic flow path 304. If three-dimensional fluidic check device 200 is held to a light source, light would not be seen between first plurality of fins 302 and second plurality of fins 306.

In view 500, allowance surface 502 of housing 202 is visible. Allowance surface 502 is the nearest of allowance surfaces 308 to first end 206 of housing 202. Allowance surface 504 of elongated center body 204 is visible in view 500. Allowance surface 504 is the nearest of allowance surfaces 310 to first end 206 of housing 202.

Figure 6:
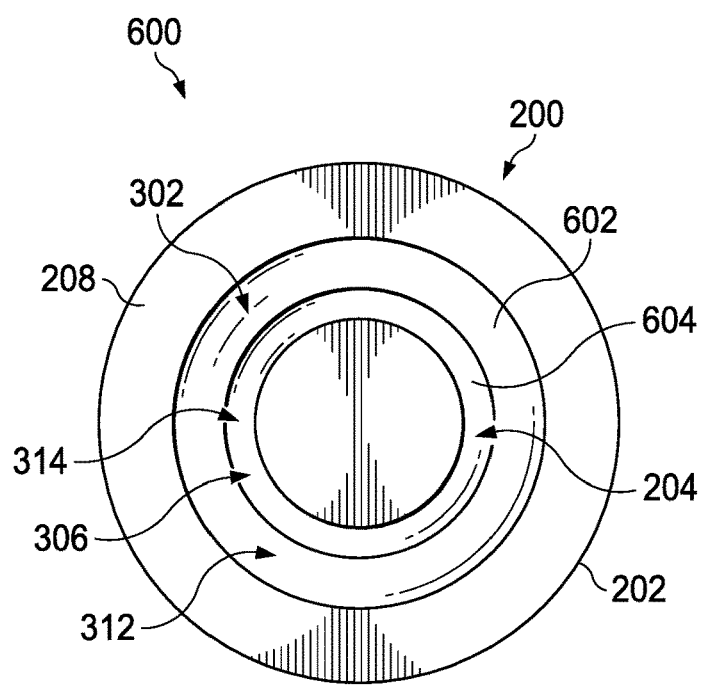
FIG. 6 is an illustration of a bottom view of a three-dimensional fluidic check device in accordance with an illustrative embodiment.

Turning now to FIG. 6, an illustration of a bottom view of a three-dimensional fluidic check device is depicted in accordance with an illustrative embodiment. View 600 is a view of three-dimensional fluidic check device 200 from direction 6 of FIG. 2. View 600 is a view looking into second end 208 towards first end 206 of housing 202.

In view 600, restrictive surface 602 of housing 202 is visible. Restrictive surface 602 is the nearest of restrictive surfaces 312 to second end 208 of housing 202. Restrictive surface 604 of elongated center body 204 is visible in view 600. Restrictive surface 604 is the nearest of restrictive surfaces 314 to second end 208 of housing 202.

Figure 7:
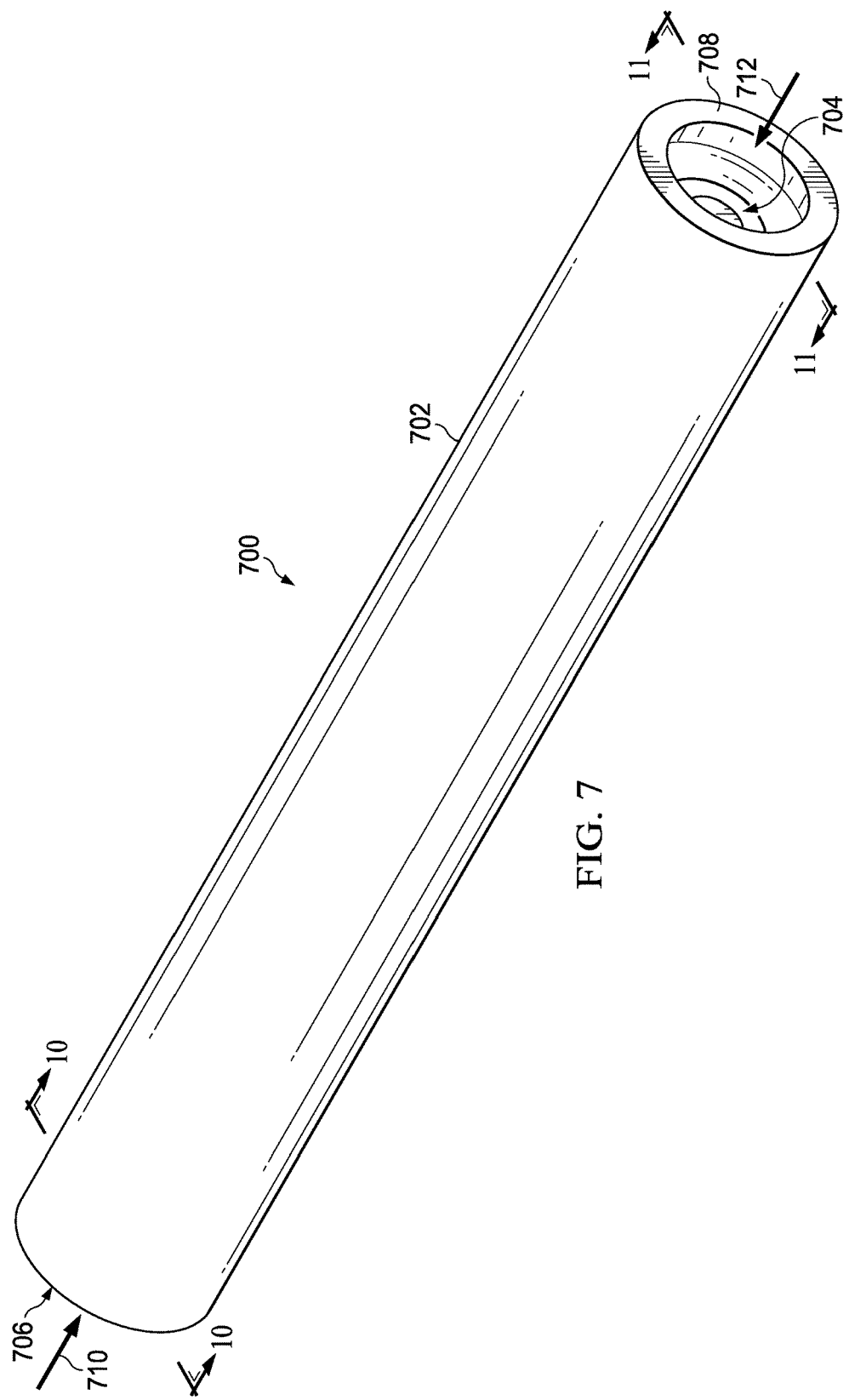
FIG. 7 is an illustration of an external view of another three-dimensional fluidic check device in accordance with an illustrative embodiment.

Turning now to FIG. 7, an illustration of an external view of another three-dimensional fluidic check device is depicted in accordance with an illustrative embodiment. Three-dimensional fluidic check device 700 is a physical implementation of three-dimensional fluidic check device 102 of FIG. 1.

Three-dimensional fluidic check device 700 comprises housing 702 and elongated center body 704. In some illustrative examples, three-dimensional fluidic check device 200 is a monolithic three-dimensional fluidic check device. In these illustrative examples, housing 202 and elongated center body 204 are integrally formed.

In some illustrative examples, housing 702 is monolithic. In some illustrative examples, elongated center body 704 is monolithic.

Elongated center body 704 is joined to housing 702 such that elongated center body 704 is stationary within housing 702. Elongated center body 704 is joined to housing 702 such that elongated center body 704 is stationary relative to a flow of a fluid (not depicted). Housing 702 has first end 706 and second end 708.

Three-dimensional fluidic check device 700 is configured such that a flow of fluid (not depicted) is allowed in flow direction 710. Three-dimensional fluidic check device 700 is configured such that a flow of fluid (not depicted) is restricted in checked direction 712.

Three-dimensional fluidic check device 700 has considerably different dimensions than three-dimensional fluidic check device 200 of FIGS. 2-6. Three-dimensional fluidic check device 700 is elongated, resembling a straw.

Figure 8:
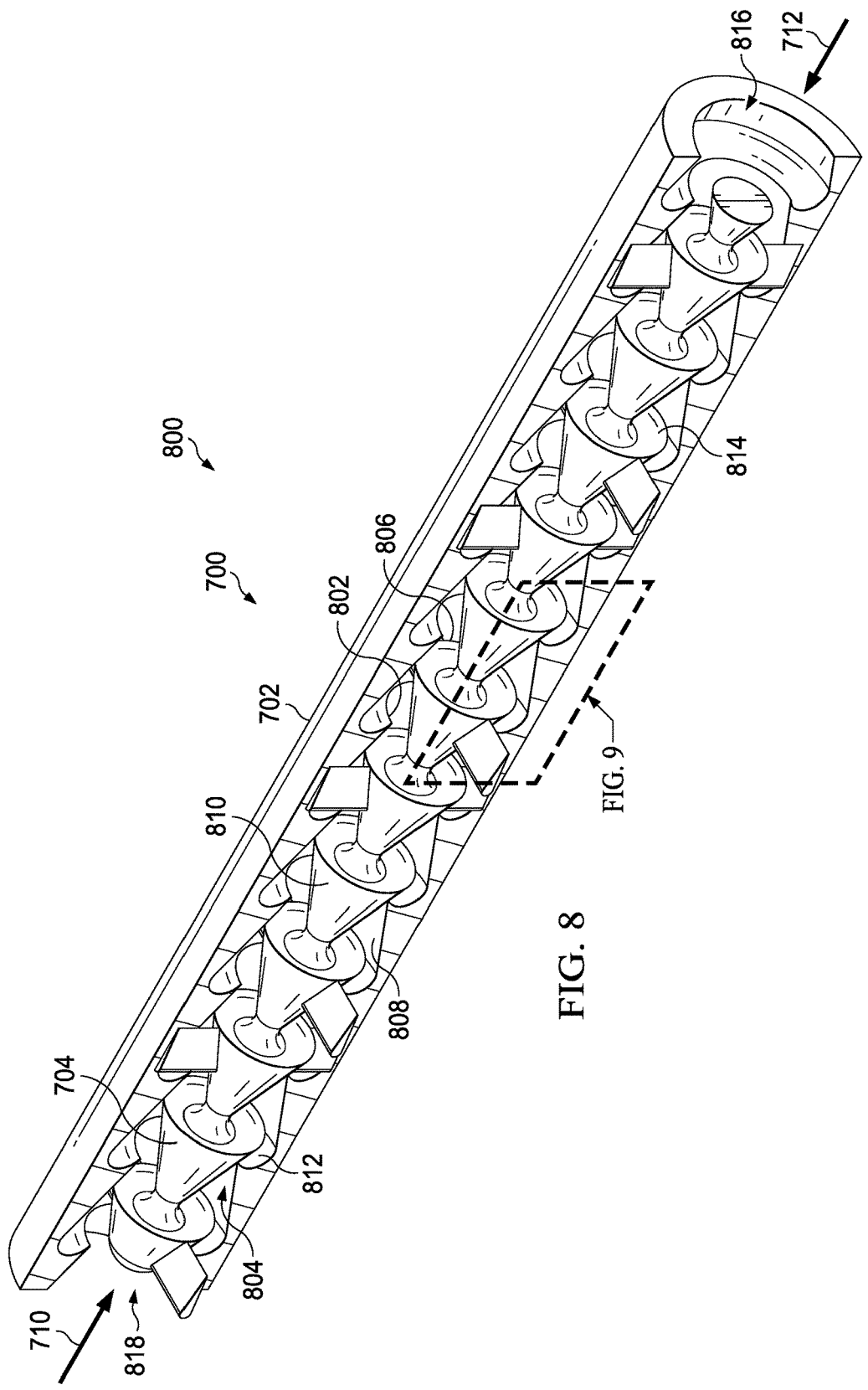
FIG. 8 is an illustration of a perspective cross-sectional view of a three-dimensional fluidic check device in accordance with an illustrative embodiment.

Turning now to FIG. 8, an illustration of a perspective cross-sectional view of a three-dimensional fluidic check device is depicted in accordance with an illustrative embodiment. View 800 is a cross-sectional view of three-dimensional fluidic check device 700 of FIG. 7.

Housing 702 of three-dimensional fluidic check device 700 has first plurality of fins 802 extending from housing 702 into fluidic flow path 804. First plurality of fins 802 is integral to housing 702. Fluidic flow path 804 is formed by housing 702 and elongated center body 704. Housing 702 contains fluidic flow path 804. Elongated center body 704 is surrounded by fluidic flow path 804.

Fluidic flow path 804 is formed and bounded by housing 702 including first plurality of fins 802 and elongated center body 704 including second plurality of fins 806. As depicted, no other structures are within fluidic flow path 804.

Elongated center body 704 comprises second plurality of fins 806 extending from elongated center body 704 into fluidic flow path 804. Second plurality of fins 806 is integral to elongated center body 704. First plurality of fins 802 and second plurality of fins 806 are configured to allow flow of a fluid (not depicted) in flow direction 710 through housing 702 and to restrict flow of the fluid (not depicted) in checked direction 712. As identified as gap 918 on FIG. 9 below, a gap is present between first plurality of fins 802 and second plurality of fins 806.

First plurality of fins 802 and second plurality of fins 806 are configured to control pressure drops through three-dimensional fluidic check device 700. In some illustrative examples, first plurality of fins 802 and second plurality of fins 806 are configured to minimize the pressure drop in flow direction 710 while maximizing the pressure drop in checked direction 712 depending on the Reynolds number and viscosity of a fluid (not depicted) passing though three-dimensional fluidic check device 700.

First plurality of fins 802 has allowance surfaces 808. As depicted in the perspective cross-sectional view of view 800, allowance surfaces 808 are linear surfaces. As depicted, allowance surfaces 808 are inverted conical surfaces. In other illustrative examples, allowance surfaces 808 may have a constant curvature, a varying curvature, or other non-linear shape in a perspective cross-sectional view. Allowance surfaces 808 allow the flow of fluid in flow direction 710. As depicted, allowance surfaces 808 are all substantially the same. In some other illustrative examples, allowance surfaces 808 may have a plurality of geometries. In some illustrative examples, allowance surfaces 808 may have different geometries moving from first end 706 to second end 708. For example, an angle of allowance surfaces 808 relative to housing 702 may change by moving from first end 706 to second end 708.

Second plurality of fins 806 has allowance surfaces 810. As depicted in the perspective cross-sectional view of view 800, allowance surfaces 810 are linear surfaces. As depicted, allowance surfaces 810 are conical surfaces. In other illustrative examples, allowance surfaces 810 may have a constant curvature, a varying curvature, or other non-linear shape in a perspective cross-sectional view. Allowance surfaces 810 allow the flow of fluid in flow direction 710. As depicted, allowance surfaces 810 are all substantially the same. In some other illustrative examples, allowance surfaces 810 may have a plurality of geometries. In some illustrative examples, allowance surfaces 810 may have different geometries moving from first end 706 to second end 708. For example, an angle of allowance surfaces 810 relative to housing 702 may change moving from first end 706 to second end 708.

In some illustrative examples, allowance surfaces 808 and allowance surfaces 810 are substantially the same. Allowance surfaces 808 and allowance surfaces 810 are configured to work together to allow for a flow of fluid.

First plurality of fins 802 has restrictive surfaces 812. As depicted, restrictive surfaces 812 are concave curvatures facing second end 708 of housing 702. Restrictive surfaces 812 restrict the flow of fluid in checked direction 712. As depicted, restrictive surfaces 812 are all substantially the same. In some other illustrative examples, restrictive surfaces 812 may have a plurality of geometries. In some illustrative examples, restrictive surfaces 812 may have different geometries moving from first end 706 to second end 708.

Second plurality of fins 806 has restrictive surfaces 814. As depicted, restrictive surfaces 814 are concave curvatures facing second end 708 of housing 702. Restrictive surfaces 814 restrict the flow of fluid in checked direction 712. As depicted, restrictive surfaces 814 are all substantially the same. In some other illustrative examples, restrictive surfaces 814 may have a plurality of geometries. In some illustrative examples, restrictive surfaces 814 may have different geometries moving from first end 706 to second end 708.

Restrictive surfaces 812 and restrictive surfaces 814 are configured to control pressure drops in three-dimensional fluidic check device 700. In some illustrative examples, restrictive surfaces 812 and restrictive surfaces 814 are configured to minimize the pressure drop in flow direction 710 while maximizing the pressure drop in checked direction 712 depending on the Reynolds number and viscosity of a fluid (not depicted) passing though three-dimensional fluidic check device 700.

Restrictive surfaces 812 and restrictive surfaces 814 are configured to generate the Coanda effect in fluid flow from second end 708 to first end 706. The Coanda effect directs the momentum of the fluid. Directing the momentum of the fluid using housing 702 and elongated center body 704 positioned within and extending along fluidic flow path 804 restricts the flow of the fluid from second opening 816 to first opening 818.

The Coanda effect biases the flow of fluid (not depicted) in checked direction 712 towards at least one of restrictive surfaces 812 or restrictive surfaces 814 of three-dimensional fluidic check device 700. The geometry of first plurality of fins 802 and the geometry of second plurality of fins 806 are configured to bias the flow of the fluid (not depicted) in checked direction 712 towards at least one of restrictive surfaces 812 or restrictive surfaces 814 of three-dimensional fluidic check device 700.

Due to the Coanda effect, the geometry of first plurality of fins 802, and the geometry of second plurality of fins 806, additional structures to direct fluid are not present in fluidic flow path 804. Flow of fluid in checked direction 712 is biased towards at least one of restrictive surfaces 812 or restrictive surfaces 814 of three-dimensional fluidic check device 700 using only the geometry of elongated center body 704 and the geometry of housing 702.

Figure 9:
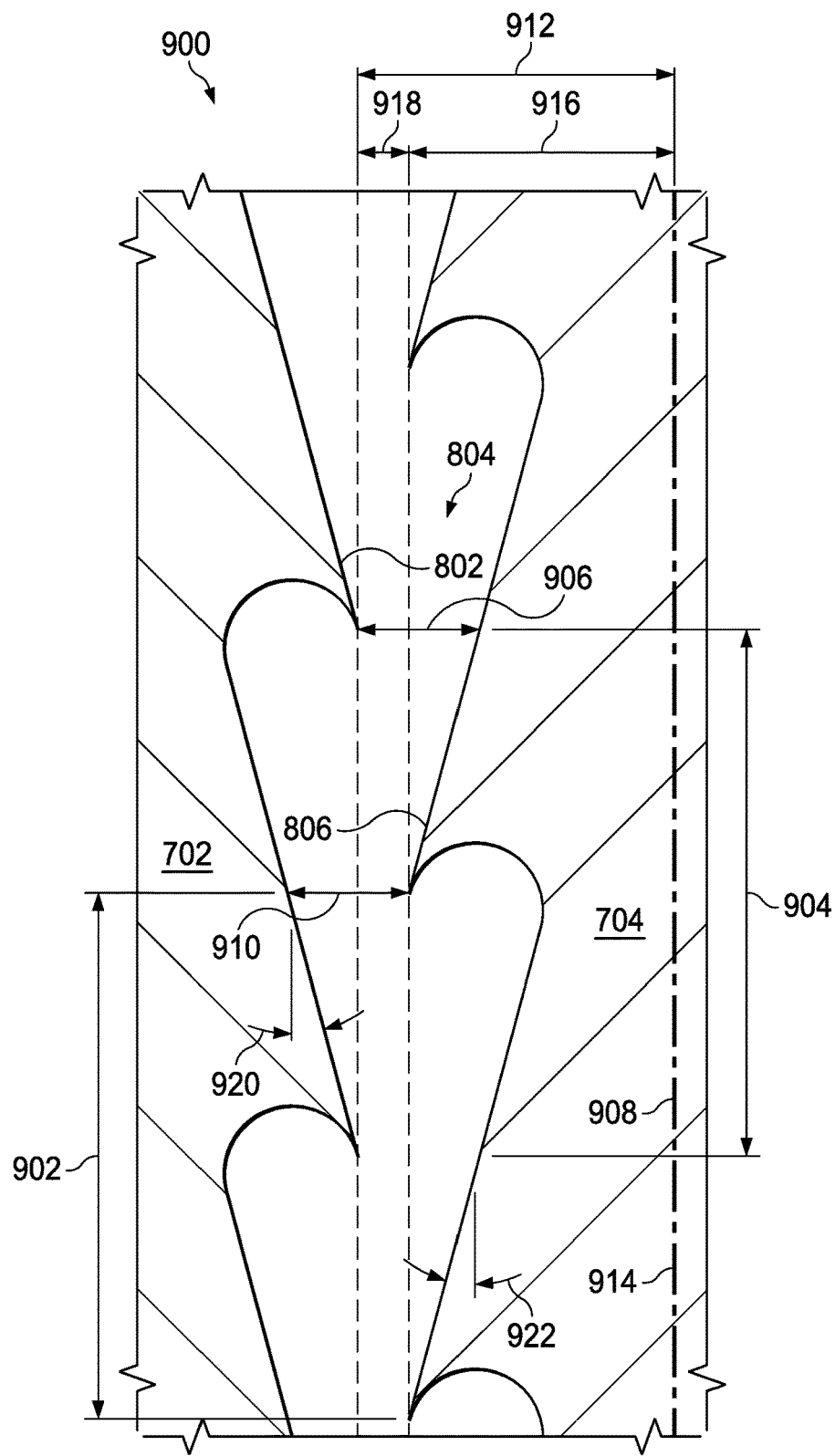
FIG. 9 is an illustration of a cross-sectional view of a three-dimensional fluidic check device in accordance with an illustrative embodiment.

Turning now to FIG. 9, an illustration of a cross-sectional view of a three-dimensional fluidic check device is depicted in accordance with an illustrative embodiment. View 900 is a view of first plurality of fins 802 and second plurality of fins 806 within box 9 of FIG. 8.

The geometry of first plurality of fins 802 and the geometry of second plurality of fins 806 are configured based on the desired flow of a fluid, the type of fluid, and generating the Coanda effect. First plurality of fins 802 and second plurality of fins 806 have a plurality of variables that may be changed.

Length 902 is a distance between points of first plurality of fins 802. In this illustrative example, each of first plurality of fins 802 has the same geometry. Length 902 for each of first plurality of fins 802 is the same. Length 902 may be referred to as a "base unit length."

Length 904 is a distance between points of second plurality of fins 806. In this illustrative example, each of second plurality of fins 806 has the same geometry. Length 904 for each of second plurality of fins 806 is the same. Length 904 may be referred to as a "base unit length."

In this illustrative example, length 902 and length 904 are substantially the same. In some illustrative examples, length 902 and length 904 may be different.

First distance 906 is from a point of one of first plurality of fins 802 to elongated center body 704 measured perpendicular to centerline 908 extending through fluidic flow path 804. Second distance 910 is from a point of one of second plurality of fins 806 to housing 702 measured perpendicular to centerline 908 extending through fluidic flow path 804. In some illustrative examples, first distance 906 is substantially the same as second distance 910.

A difference between first measurement 912 from a point of one of first plurality of fins 802 to centerline 914 of elongated center body 704 and second measurement 916 from a point of one of second plurality of fins 806 to centerline 914 of elongated center body 704 is a variable. In some illustrative examples, the difference between first measurement 912 and second measurement 916 is positive. When the difference is positive, gap 918 exists between first plurality of fins 802 and second plurality of fins 806 as depicted. In other illustrative examples, such as in FIG. 4, the difference between first measurement 912 and second measurement 916 is negative.

As depicted, centerline 908 of fluidic flow path 804 and centerline 914 of elongated center body 704 coincide. In this illustrative example, elongated center body 704 is centered within fluidic flow path 804. However, in other non-depicted illustrative examples, centerline 908 and centerline 914 may be different when elongated center body 704 is not completely centered within fluidic flow path 804. For example, centerline 908 and centerline 914 may be different when three-dimensional fluidic check device 700 is curved.

Each of allowance surfaces 808 of first plurality of fins 802 has angle 920. Angle 920 affects the flow of fluid through three-dimensional fluidic check device 700. Angle 920 also allows for gap 918 between first plurality of fins 802 and second plurality of fins 806. As depicted, angle 920 is approximately 20 degrees. Angle 920 is selected taking into account the characteristics of the fluid and the characteristics of the flow including the viscosity of the fluid, temperature of the fluid, speed of flow, Reynolds number of the fluid, and any other desirable fluid or flow features. For example, angle 920 may be increased as the speed of flow is reduced.

As depicted, each of allowance surfaces 808 has the same angle, angle 920. In other non-depicted examples, at least one of allowance surfaces 808 has a different angle than angle 920. In some non-depicted illustrative examples, each of allowance surfaces 808 has a different angle from each other allowance surface of allowance surfaces 808.

Each of allowance surfaces 810 of second plurality of fins 806 has angle 922. Angle 922 affects the flow of fluid through three-dimensional fluidic check device 700. Angle 922 also allows for gap 918 between first plurality of fins 802 and second plurality of fins 806. As depicted, angle 922 is approximately 20 degrees. Angle 922 is selected taking into account the characteristics of the fluid and the characteristics of the flow including the viscosity of the fluid, temperature of the fluid, speed of flow, Reynolds number of the fluid, and any other desirable fluid or flow features.

As depicted, each of allowance surfaces 810 has the same angle, angle 922. In other non-depicted examples, at least one of allowance surfaces 810 has a different angle than angle 922. In some non-depicted illustrative examples, each of allowance surfaces 810 has a different angle from each other allowance surface of allowance surfaces 810.

Figure 10:
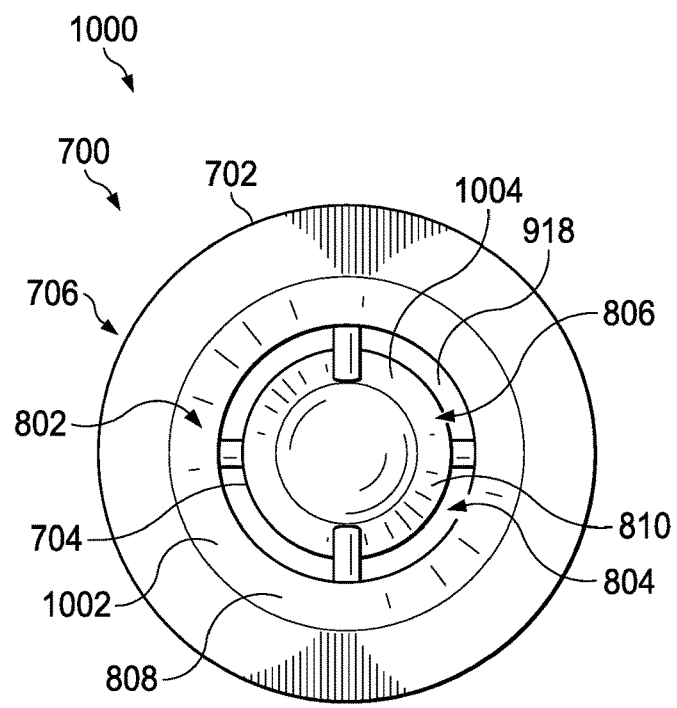
FIG. 10 is an illustration of a top view of a three-dimensional fluidic check device in accordance with an illustrative embodiment.

Turning now to FIG. 10, an illustration of a top view of a three-dimensional fluidic check device is depicted in accordance with an illustrative embodiment. View 1000 is a view of three-dimensional fluidic check device 700 from direction 10 of FIG. 7. View 1000 is a view looking into first end 706 towards second end 708 of FIG. 7.

As can be seen in view 1000, fluidic flow path 804 includes a straight path from first end 706 to second end 708. Gap 918 is between first plurality of fins 802 and second plurality of fins 806 creating a straight path for fluid within fluidic flow path 804. If three-dimensional fluidic check device 700 is held to a light source, light could be seen between first plurality of fins 802 and second plurality of fins 806.

In view 1000, allowance surface 1002 of housing 702 is visible. Allowance surface 1002 is the nearest of allowance surfaces 808 of FIG. 8 to first end 706 of housing 702. Allowance surface 1004 of elongated center body 704 is visible in view 1000. Allowance surface 1004 is the nearest of allowance surfaces 810 to first end 706 of housing 702.

Figure 11:
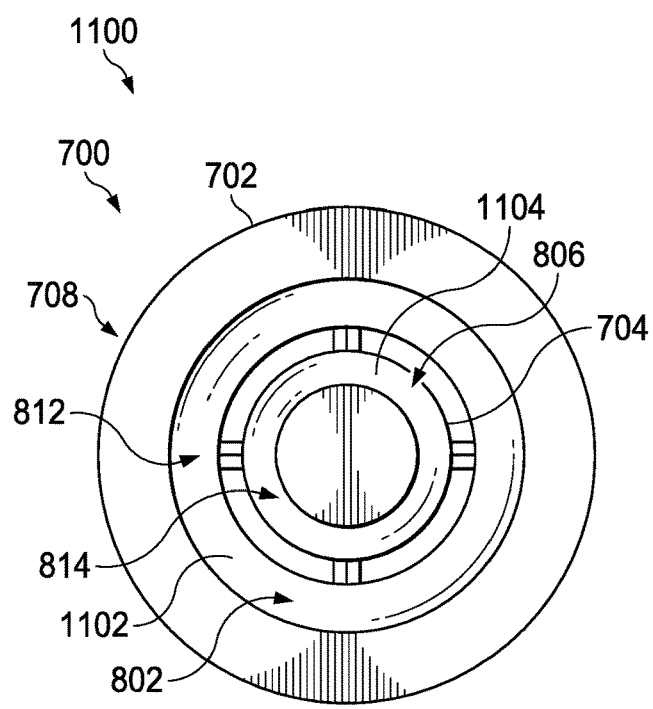
FIG. 11 is an illustration of a bottom view of a three-dimensional fluidic check device in accordance with an illustrative embodiment.

Turning now to FIG. 11, an illustration of a bottom view of a three-dimensional fluidic check device is depicted in accordance with an illustrative embodiment. View 1100 is a view of three-dimensional fluidic check device 700 from direction 11 of FIG. 7. View 1100 is a view looking into second end 708 of towards first end 706 of housing 702 seen in FIGS. 7 and 10.

In view 1100, restrictive surface 1102 of housing 702 is visible. Restrictive surface 1102 is the nearest of restrictive surfaces 812 to second end 708 of housing 702. Restrictive surface 1104 of elongated center body 704 is visible in view 1100. Restrictive surface 1104 is the nearest of restrictive surfaces 814 to second end 708 of housing 702.

Figure 12:
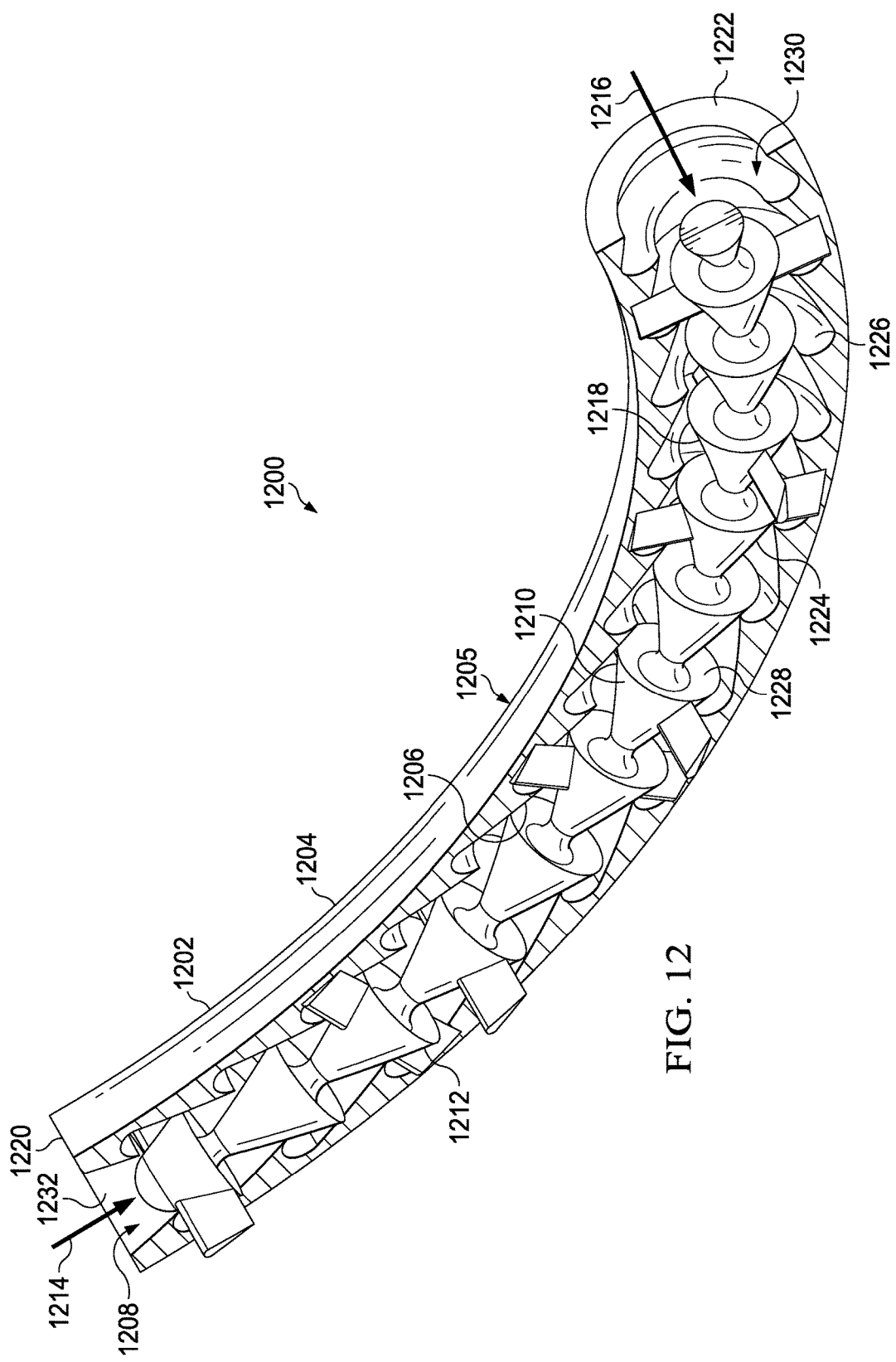
FIG. 12 is an illustration of a cross-sectional view of another three-dimensional fluidic check device in accordance with an illustrative embodiment.

Turning now to FIG. 12, an illustration of a cross-sectional view of another three-dimensional fluidic check device is depicted in accordance with an illustrative embodiment. View 1200 is a cross-sectional view of three-dimensional fluidic check device 1202. Three-dimensional fluidic check device 1202 is a physical implementation of three-dimensional fluidic check device 102 of FIG. 1.

In some illustrative examples, three-dimensional fluidic check device 1202 is a monolithic three-dimensional fluidic check device. In these illustrative examples, housing 1204 and elongated center body 1210 are integrally formed.

As depicted, three-dimensional fluidic check device 1202 is curved. Housing 1204 of three-dimensional fluidic check device 1202 is curved. In some illustrative examples, housing 1204 and elongated center body 1210 are formed of a material configured to maintain shape 1205 of housing 1204. For example, shape 1205 may be an originally manufactured shape of housing 1204. In this example, the material of housing 1204 and elongated center body 1210 may be selected to provide sufficient rigidity to maintain shape 1205. In this example, three-dimensional fluidic check device 1202 is manufactured with shape 1205.

In some illustrative examples, housing 1204 and elongated center body 1210 are formed of a material configured to allow for changing shape 1205 of housing 1204. When the material is flexible enough to change shape 1205 of housing 1204, housing 1204 may be bent into a desirable shape to connect to an inlet and an outlet.

In some illustrative examples, the flexible material may be polymeric material. In some illustrative examples, the flexible material is an elastomeric material such as silicone rubber. When the material is flexible, the acceptable changes to shape 1205 are dependent upon the internal geometries of housing 1204 and elongated center body 1210. In some illustrative examples, internal geometries of housing 1204 and elongated center body 1210 may be configured based on expected changes to shape 1205. In some illustrative examples, housing 1204 and elongated center body 1210 are flexible, and fabricated taking into account design guidelines for at least one of the flexible material, the fluid to flow through three-dimensional fluidic check device 1202, expected changes to shape 1205, or any other design guidelines.

The material, rigid or flexible, may be formed using any desirable method. In some illustrative examples, a material may be formed into three-dimensional fluidic check device 1202 using additive manufacturing. For example, three-dimensional fluidic check device 1202 may be printed on three-dimensional printers. In some illustrative examples, a material may be formed into three-dimensional fluidic check device 1202 using a number of molds.

Housing 1204 of three-dimensional fluidic check device 1202 has first plurality of fins 1206 extending from housing 1204 into fluidic flow path 1208. First plurality of fins 1206 is integral to housing 1204. Fluidic flow path 1208 is formed by housing 1204 and elongated center body 1210. Housing 1204 contains fluidic flow path 1208. Elongated center body 1210 is surrounded by fluidic flow path 1208.

Fluidic flow path 1208 is formed and bounded by housing 1204 including first plurality of fins 1206 and elongated center body 1210 including second plurality of fins 1212. As depicted, no other structures are within fluidic flow path 1208.

Elongated center body 1210 comprises second plurality of fins 1212 extending from elongated center body 1210 into fluidic flow path 1208. Second plurality of fins 1212 is integral to elongated center body 1210. First plurality of fins 1206 and second plurality of fins 1212 are configured to allow flow of a fluid (not depicted) in flow direction 1214 through housing 1204 and to restrict the flow of the fluid (not depicted) in checked direction 1216. As depicted, first plurality of fins 1206 overlaps second plurality of fins 1212.

First plurality of fins 1206 has allowance surfaces 1218. As depicted, allowance surfaces 1218 are substantially straight surfaces. In other illustrative examples, allowance surfaces 1218 may have a constant curvature, a varying curvature, or other non-planar shape. Allowance surfaces 1218 allow the flow of fluid in flow direction 1214. As depicted, allowance surfaces 1218 are all substantially the same. In some other illustrative examples, allowance surfaces 1218 may have a plurality of geometries. In some illustrative examples, allowance surfaces 1218 may have different geometries moving from first end 1220 to second end 1222. For example, an angle of the allowance surfaces 1218 relative to housing 1204 may change moving from first end 1220 to second end 1222.

Second plurality of fins 1212 has allowance surfaces 1224. As depicted, allowance surfaces 1224 are substantially straight surfaces. In other illustrative examples, allowance surfaces 1224 may have a constant curvature, a varying curvature, or other non-planar shape. Allowance surfaces 1224 allow the flow of fluid in flow direction 1214. As depicted, allowance surfaces 1224 are all substantially the same. In some other illustrative examples, allowance surfaces 1224 may have a plurality of geometries. In some illustrative examples, allowance surfaces 1224 may have different geometries moving from first end 1220 to second end 1222. For example, an angle of allowance surfaces 1224 relative to housing 1204 may change moving from first end 1220 to second end 1222.

In some illustrative examples, allowance surfaces 1218 and allowance surfaces 1224 are substantially the same. Allowance surfaces 1218 and allowance surfaces 1224 are configured to work together to allow for a flow of fluid.

First plurality of fins 1206 has restrictive surfaces 1226. As depicted, restrictive surfaces 1226 are concave curvatures facing second end 1222 of housing 1204. Restrictive surfaces 1226 restrict the flow of fluid in checked direction 1216. As depicted, restrictive surfaces 1226 are all substantially the same. In some other illustrative examples, restrictive surfaces 1226 may have a plurality of geometries. In some illustrative examples, restrictive surfaces 1226 may have different geometries moving from first end 1220 to second end 1222.

Second plurality of fins 1212 has restrictive surfaces 1228. As depicted, restrictive surfaces 1228 are concave curvatures facing second end 1222 of housing 1204. Restrictive surfaces 1228 restrict the flow of fluid in checked direction 1216. As depicted, restrictive surfaces 1228 are all substantially the same. In some other illustrative examples, restrictive surfaces 1228 may have a plurality of geometries. In some illustrative examples, restrictive surfaces 1228 may have different geometries moving from first end 1220 to second end 1222.

Restrictive surfaces 1226 and restrictive surfaces 1228 are configured to generate the Coanda effect in fluid flow from second end 1222 to first end 1220. The Coanda effect directs the momentum of the fluid. Directing the momentum of the fluid using housing 1204 and elongated center body 1210 positioned within and extending along fluidic flow path 1208 restricts the flow of the fluid from second opening 1230 to first opening 1232.

Due to the Coanda effect, the geometry of first plurality of fins 802, and the geometry of second plurality of fins 806, additional structures to direct fluid are not present in fluidic flow path 804. Flow of fluid in checked direction 712 is biased towards at least one of restrictive surfaces 812 or restrictive surfaces 814 of three-dimensional fluidic check device 700 using only the geometry of elongated center body 704 and the geometry of housing 702.

Figure 13:
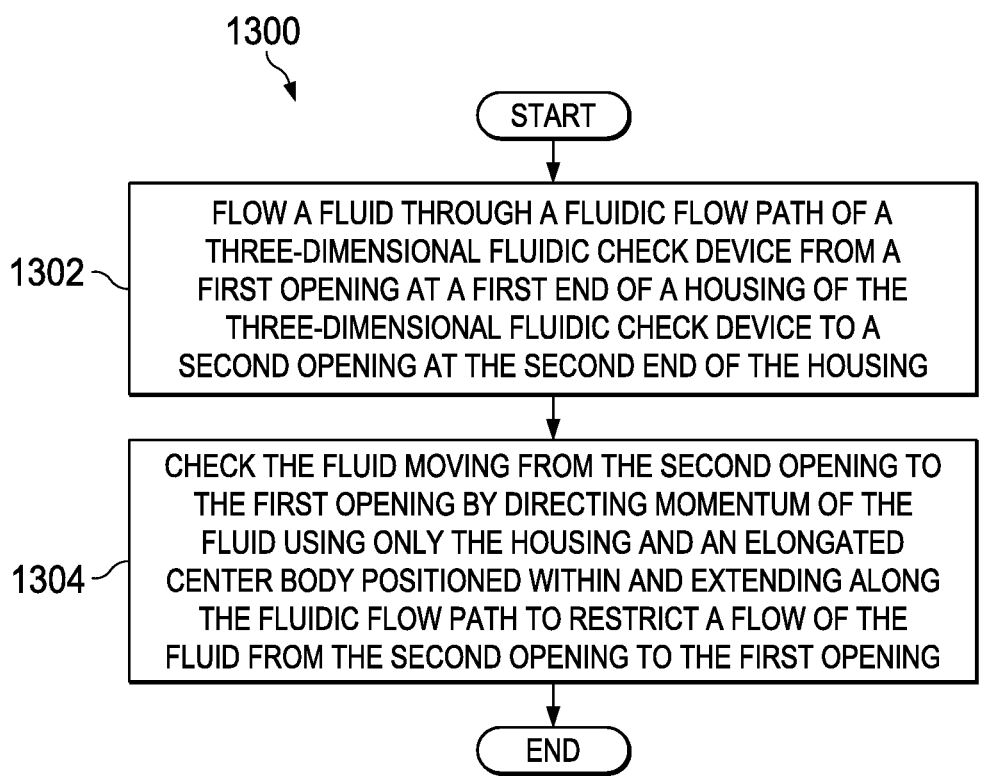
FIG. 13 is an illustration of a flowchart of a method for controlling a flow of fluid in accordance with an illustrative embodiment.

Turning now to FIG. 13, an illustration of a flowchart of a method for controlling a flow of fluid is depicted in accordance with an illustrative embodiment. Method 1300 may be implemented using three-dimensional fluidic check device 102 of FIG. 1. Method 1300 may be implemented using three-dimensional fluidic check device 200 of FIGS. 2-6. Method 1300 may be implemented using three-dimensional fluidic check device 700 of FIGS. 7-11. Method 1300 may be implemented using three-dimensional fluidic check device 1202 of FIG. 12.

Method 1300 flows a fluid through a fluidic flow path of a three-dimensional fluidic check device from a first opening at a first end of a housing of the three-dimensional fluidic check device to a second opening at a second end of the housing (operation 1302). Method 1300 checks the fluid from moving from the second opening to the first opening by directing the momentum of the fluid using only the housing and an elongated center body positioned within and extending along the fluidic flow path to restrict a flow of the fluid from the second opening to the first opening (operation 1304). Afterwards, the method terminates.

In some illustrative examples, checking the fluid from moving from the second opening to the first opening by directing the momentum of the fluid comprises directing momentum of the fluid to restrict a flow of the fluid using a first plurality of fins extending from the housing into the fluidic flow path and a second plurality of fins extending from the elongated center body into the fluidic flow path. In some further illustrative examples, directing the momentum of the fluid to restrict a flow of the fluid using a first plurality of fins extending from the housing into the fluidic flow path and a second plurality of fins extending from the elongated center body into the fluidic flow path comprises directing the momentum of the fluid using a respective concave curvature of each of the first plurality of fins and each of the second plurality of fins facing the second opening.

The flowcharts and block diagrams in the different depicted illustrative embodiments illustrate the architecture, functionality, and operation of some possible implementations of apparatuses and methods in an illustrative embodiment. In this regard, each block in the flowcharts or block diagrams may represent a module, a segment, a function, and/or a portion of an operation or step.

In some alternative implementations of an illustrative embodiment, the function or functions noted in the blocks may occur out of the order noted in the Figures. For example, in some cases, two blocks shown in succession may be executed substantially concurrently, or the blocks may sometimes be performed in the reverse order, depending upon the functionality involved. Also, other blocks may be added, in addition to the illustrated blocks, in a flowchart or block diagram. For example, in some illustrative examples, method 1300 further comprises changing a shape of the housing by bending the three-dimensional fluidic check device.

A three-dimensional fluidic check device is described. The illustrative examples of a three-dimensional fluidic check device are more compact and have less pressure loss than conventional two-dimensional check valves. Additive manufacturing techniques enable manufacturing an elongated center body inside the housing of the three-dimensional fluidic check device.

This three-dimensional valve uses the geometry of the valve to create a nozzle whose down stream flow exploits the Coanda effect at the device's internal surfaces to direct the fluid into turning passages to use the momentum of the flow in the turning passages against the momentum of center flow trying to exit the device. This creates a staged fluid dynamic check valve.

For systems with multiple sources of fluidic flow, the valve will work to prevent back flow into already emptied sources. The specially designed shell and guide vanes result in a three-dimensional one-way check valve. The guide vanes have a socket that redirects the fluid (e.g., uses the momentum) to impede fluid flow in a reverse direction while allowing the fluid to flow relatively freely in a flow direction.

The description of the different illustrative embodiments has been presented for purposes of illustration and description, and is not intended to be exhaustive or limited to the embodiments in the form disclosed. Many modifications and variations will be apparent to those of ordinary skill in the art. Further, different illustrative embodiments may provide different features as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A monolithic three-dimensional fluidic check device comprising:
    a housing surrounding a fluidic flow path and having a first opening at a first end of the housing and a second opening at a second end of the housing; and
    an elongated center body positioned within and extending along the fluidic flow path, wherein the elongated center body is stationary relative to a flow of fluid,
    wherein the housing comprises a first plurality of fins extending from the housing into the fluidic flow path, wherein the first plurality of fins is integral to the housing,
    wherein the elongated center body comprises a second plurality of fins extending from the elongated center body into the fluidic flow path, wherein the second plurality of fins is integral to the elongated center body, and
    wherein each of the first plurality of fins and each of the second plurality of fins has a respective concave curvature facing the second end.

2. The monolithic three-dimensional fluidic check device of claim 1, wherein the first plurality of fins and the second plurality of fins are configured to create a flow direction from the first end to the second end and a checked direction from the second end to the first end.

3. The monolithic three-dimensional fluidic check device of claim 1, wherein each of the first plurality of fins and each of the second plurality of fins has a respective substantially straight surface facing the first end.

4. The monolithic three-dimensional fluidic check device of claim 1, wherein a first distance from a point of one of the first plurality of fins to the elongated center body measured perpendicular to a centerline extending through the fluidic flow path is substantially the same as a second distance from a point of one of the second plurality of fins to the housing measured perpendicular to the centerline extending through the fluidic flow path.

5. The monolithic three-dimensional fluidic check device of claim 1, wherein the first plurality of fins and the second plurality of fins are configured to produce a Coanda effect for fluid moving from the second end to the first end within the fluidic flow path.

6. The monolithic three-dimensional fluidic check device of claim 1, wherein a difference between a first measurement from a point of one of the first plurality of fins to a centerline of the elongated center body and a second measurement from a point of one of the second plurality of fins to the centerline of the elongated center body is negative.

7. The monolithic three-dimensional fluidic check device of claim 1, wherein a difference between a first measurement from a point of one of the first plurality of fins to a centerline of the elongated center body and a second measurement from a point of one of the second plurality of fins to the centerline of the elongated center body is positive.

8. The monolithic three-dimensional fluidic check device of claim 1, wherein the fluidic flow path is formed and bounded by the housing including the first plurality of fins and the elongated center body including the second plurality of fins.

9. The monolithic three-dimensional fluidic check device of claim 1, wherein the housing and the elongated center body are formed of a material configured to allow changing a shape of the housing.

10. A three-dimensional fluidic check device comprising:
    a housing containing a fluidic flow path formed by the housing and an elongated center body, wherein the housing comprises a first plurality of fins extending from the housing into the fluidic flow path; and
    the elongated center body surrounded by the fluidic flow path, wherein the elongated center body comprises a second plurality of fins extending from the elongated center body into the fluidic flow path, wherein the first plurality of fins and the second plurality of fins are configured to allow flow of a fluid in a flow direction through the housing and to restrict flow of the fluid in a checked direction, wherein each of the first plurality of fins and each of the second plurality of fins has a respective restrictive surface restricting flow of fluid in the checked direction, and wherein each respective restrictive surface is a concave curvature.

11. The three-dimensional fluidic check device of claim 10, wherein the first plurality of fins overlaps the second plurality of fins.

12. The three-dimensional fluidic check device of claim 10, wherein each of the first plurality of fins and each of the second plurality of fins has a respective allowance surface allowing flow of fluid in the flow direction.

13. A method comprising:
flowing a fluid through a fluidic flow path of a three-dimensional fluidic check device from a first opening at a first end of a housing of the three-dimensional fluidic check device to a second opening at a second end of the housing; and checking the fluid from moving from the second opening to the first opening by directing momentum of the fluid using only the housing and an elongated center body positioned within and extending along the fluidic flow path to restrict a flow of the fluid from the second opening to the first opening, wherein checking the fluid from moving from the second opening to the first opening by directing momentum of the fluid comprises directing momentum of the fluid to restrict a flow of the fluid using a first plurality of fins extending from the housing into the fluidic flow path and a second plurality of fins extending from the elongated center body into the fluidic flow path, wherein the first plurality of fins is integral to the housing and wherein the second plurality of fins is integral to the elongated center body, and wherein directing momentum of the fluid to restrict a flow of the fluid using a first plurality of fins extending from the housing into the fluidic flow path and a second plurality of fins extending from the elongated center body into the fluidic flow path comprises directing momentum of the fluid using a respective concave curvature of each of the first plurality of fins and each of the second plurality of fins facing the second opening.

14. The method of claim 13, further comprising:
changing a shape of the housing by bending the three-dimensional fluidic check device.

* * * * *

UNITED STATES PATENT AND TRADEMARK OFFICE
CERTIFICATE OF CORRECTION

PATENT NO. : 10,245,586 B2  
APPLICATION NO. : 15/668503  
DATED : April 2, 2019  
INVENTOR(S) : Gilbert et al.

Page 1 of 1

It is certified that error appears in the above-identified patent and that said Letters Patent is hereby corrected as shown below:

In the Claims

Column 22, Line 6, Claim 13 change "a flow of the fluid" to -- the flow of the fluid --
    Line 13, change "a flow of the fluid" to -- the flow of the fluid; --
    Line 14, change "a first plurality of fins" to -- the first plurality of fins; --
    Line 15, change "a second plurality of fins" to -- the second plurality of fins. --

Signed and Sealed this
Eighteenth Day of June, 2019

Andrei Iancu
*Director of the United States Patent and Trademark Office*